(12) United States Patent
Proksa

(10) Patent No.: US 9,901,311 B2
(45) Date of Patent: Feb. 27, 2018

(54) IMAGING APPARATUS

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 27 days.

(21) Appl. No.: 14/895,384

(22) PCT Filed: Jun. 17, 2014

(86) PCT No.: PCT/EP2014/062608
§ 371 (c)(1),
(2) Date: Dec. 2, 2015

(87) PCT Pub. No.: WO2014/206794
PCT Pub. Date: Dec. 31, 2014

(65) Prior Publication Data
US 2016/0113597 A1  Apr. 28, 2016

(30) Foreign Application Priority Data
Jun. 26, 2013 (EP) ..................... 13173758

(51) Int. Cl.
*A61B 6/03* (2006.01)
*A61B 6/00* (2006.01)

(52) U.S. Cl.
CPC .............. *A61B 6/035* (2013.01); *A61B 6/032* (2013.01); *A61B 6/405* (2013.01); *A61B 6/4291* (2013.01); *A61B 6/5205* (2013.01); *A61B 6/542* (2013.01)

(58) Field of Classification Search
CPC .. A61B 6/02; A61B 6/03; A61B 6/025; A61B 6/032; A61B 6/037; G06T 11/003;
(Continued)

(56) References Cited

U.S. PATENT DOCUMENTS 5,485,494 A  1/1996 Williams et al.
5,625,662 A  4/1997 Toth et al.
(Continued)

FOREIGN PATENT DOCUMENTS

DE  102009051633  5/2011
DE  102011054114  4/2012
(Continued)

OTHER PUBLICATIONS

Erdogan, et al., "Ordered subsets algorithms for transmission tomography", Phys. Med. Biol. 44 (1999) 2835-2851.

*Primary Examiner* — Don Wong

(57) ABSTRACT

The invention relates to an X-ray imaging apparatus and a method, particularly to a CT scanner (100) for generating sectional images of an object such as the body (P) of a patient. A given desired angular intensity distribution ($I_{des}$) is reproduced by emitting X-rays (X) in emission angle intervals (EAI) only, wherein the angular distribution of these emission angle intervals and the associated local emission intensities ($I(\alpha)$) are chosen such that they reproduce, in the angular mean, the desired angular intensity distribution ($I_{des}$). Modulation of incident X-ray flux is hence realized by the modulation of the angular sampling density. The X-ray source may preferably be realized by a grid switching tube (101).

10 Claims, 3 Drawing Sheets

(58) Field of Classification Search
CPC .... G06T 11/005; G06T 11/006; G06T 11/008; G06T 6/4233
USPC ........ 378/16, 14, 11, 97, 113, 12, 4, 21, 26, 378/108, 116
See application file for complete search history.

(56) References Cited

U.S. PATENT DOCUMENTS

| | | | |
|---|---|---|---|
| 5,696,807 A | 12/1997 | Hsieh | |
| 6,178,226 B1 | 1/2001 | Hell et al. | |
| 2001/0019599 A1 | 9/2001 | Guendel | |
| 2007/0092058 A1* | 4/2007 | Mattson | A61B 6/032 378/15 |
| 2008/0198965 A1 | 8/2008 | Popescu et al. | |
| 2010/0172475 A1 | 7/2010 | Behling | |
| 2011/0038460 A1 | 2/2011 | Grasruck et al. | |
| 2011/0080992 A1 | 4/2011 | Dafni | |
| 2011/0103552 A1 | 5/2011 | Walk | |
| 2011/0142193 A1 | 6/2011 | Frontera et al. | |
| 2012/0121063 A1 | 5/2012 | Proksa | |
| 2012/0177172 A1 | 7/2012 | Ooshima | |

FOREIGN PATENT DOCUMENTS

| | | |
|---|---|---|
| DE | 102011005115 | 9/2012 |
| EP | 2271189 | 1/2011 |
| WO | 2009115982 | 9/2009 |
| WO | 2010070583 | 6/2010 |
| WO | 20131001434 | 1/2013 |

\* cited by examiner

IMAGING APPARATUS

CROSS REFERENCE TO RELATED APPLICATIONS

This application is a national filing of PCT application Serial No. PCT/IB EP2014/062608, filed Jun. 17, 2014, published as WO 2014/206794 on Dec. 31, 2014, which claims the benefit of European Patent Application Number 13173758.7 filed Jun. 26, 2013, which is incorporated herein by reference.

FIELD OF THE INVENTION

The invention relates to an X-ray imaging apparatus such as a CT scanner and to a method for irradiating an object with X-rays from different viewing angles.

BACKGROUND OF THE INVENTION

The U.S. Pat. No. 5,696,807 discloses a CT scanner for generating images of a patient. In order to reduce the dose the patient is exposed to, the tube current of the X-ray source is modulated as a function of projection angle.

The US 2008/198965 A1 discloses an X-ray CT system including at least two X-ray sources. In order to determine the scattered radiation distribution, pre-scanning is carried out in which the X-ray sources rotate about the examination object and no radiation dose is output over the majority of the revolution, at specific pre-scan angles a dose rate is produced briefly and individually, and the received scattered radiation is measured.

SUMMARY OF THE INVENTION

It would be desirable to have means that allow for the imaging of an object with a further reduced X-ray dose.

This object is achieved by an X-ray imaging apparatus according to claim 1 and a method according to claim 2. Preferred embodiments are disclosed in the dependent claims.

According to a first aspect, the invention relates to an X-ray imaging apparatus (or "CT scanner") that is adapted to irradiate an object with X-rays from different viewing angles according to a given desired angular intensity distribution. The imaging apparatus comprises the following components:

An X-ray source for emitting X-rays towards the object (or to a location where an object can be) from different viewing angles.

A detector for detecting X-rays emitted by the X-ray source and for generating projection images of the object from said different viewing angles.

A reconstruction module for reconstructing sectional images of the object from said projection images.

A controller for controlling said X-ray source such that emissions of X-rays occur only at "emission angle intervals" separated by gaps, wherein the angular distribution of these emission angle intervals and the associated local emission intensity reproduce, in the angular mean, the desired angular intensity distribution.

Each of the above-mentioned "emission angle intervals" shall by definition comprise a range of angles $[\alpha_1, \alpha_2]$ with $\alpha_1 \leq \alpha_2$, including the case of comprising just one discrete value if $\alpha_1 = \alpha_2$. The remainder of the full 360° range of angles is constituted by the "gaps" that each lie between two emission angle intervals. The angular intervals of the gaps will typically consist of not just one discrete value but a continuous range, providing for a non-zero distance between two neighboring emission angle intervals.

The "angular distribution" of the emission angle intervals just refers to the location of these intervals on the whole 360° range of angles, i.e. it is given by the whole set of the $\alpha_1, \alpha_2$ mentioned above.

The "desired angular intensity distribution" will in general be a function that associates each viewing angle (or at least each viewing angle at which an emission can occur) to a desired value of the X-ray intensity to be emitted at this angle. It will in the following also be called "desired intensity distribution".

The "local emission intensity" is just the emission intensity occurring at the different viewing angles.

The "reproduction of the angular intensity distribution" refers to an appropriate angular averaging of emission intensities commanded by the controller, i.e. it is assumed that the reproduction has successfully been achieved if said angular average is approximately identical to the desired angular intensity distribution. In this context, "approximately" may further be defined as a deviation of the average from the desired angular intensity distribution of at most 20%, at most 15%, at most 10%, at most 5%, or at most 2% (the percentage measured with respect to the desired angular intensity distribution). An appropriate angular averaging may for example comprise the convolution of the actual angular intensity distribution (i.e. of the local emission intensities) with a given kernel or weighting function (cf. examples below).

The local emission intensity may or may not be constant within an emission angle interval. Moreover, the local emission intensity will usually not be proportional to the desired angular intensity distribution (with the same proportionality factor) over the whole range of all emission angle intervals (this would only be required if the emission angle intervals would be evenly distributed across the whole range of viewing angles and hence not contribute to a modulation of average intensities).

The detector shall be capable to detect X-rays emitted by the X-ray source, particularly X-rays that have passed through the object to be irradiated. Thus an imaging application can be realized in which projection images of the object from different viewing angles can be generated if the detector allows for a spatially resolved detection of transmitted X-rays.

The "reconstruction module" may for example be realized by dedicated electronic hardware, digital data processing hardware with associated software, or a mixture of both. It may particularly implement an iterative reconstruction of the sectional images from projection images (H. Erdogan and J. A. Fessler, "Ordered subsets algorithms for transmission tomography", Phys. Med. Biol. 44 (1999) 2835-2851). An iterative reconstruction has the advantage to be flexible with respect to the angular distribution of available projection images.

It should be noted that, for the purpose of the present application, the various "intensities" emitted by the X-ray source may for example be defined as the total X-ray energy emitted per unit time (measured e.g. in Watt).

The invention further relates to a method for generating images of an object by irradiating said object with X-rays from different viewing angles according to a given desired angular intensity distribution. The method comprises the following steps:

The emission of X-rays towards the object only from emission angle intervals that are separated by gaps, wherein the angular distribution of these emission angle intervals and the associated local emission intensity reproduce, in the angular mean, the desired angular intensity distribution.

The generation of projection images of the object by the X-rays emitted from said different viewing angles.

The reconstruction of sectional images of the object from said projection images.

The method comprises in general form the steps that can be executed with the imaging apparatus described above. Explanations given for the apparatus are therefore analogously valid for the method, too, and vice versa.

The method and the imaging apparatus have the advantage that they allow for the simultaneous fulfillment of two requirements, namely the reproduction of a desired angular intensity distribution (at least on the average) AND the application of comparably high local emission intensities. This is achieved by squeezing the necessary emissions into emission angle intervals. The fulfillment of both requirements is for example favorable in case of an imaging application, in which dosage is minimized by adherence to a desired angular intensity distribution and noise is reduced by high local emission intensities.

In the following, various preferred embodiments of the invention will be described that relate to both the imaging apparatus and the method defined above.

In one preferred embodiment, the local emission intensities within all emission angle intervals are larger than a given minimal intensity. This condition guarantees that there is always a minimal intensity or flux available for processes such as the detection of transmitted X-rays. A typical realization of this embodiment comprises that both a desired angular intensity distribution and said minimal intensity are given in advance, e.g. derived from boundary conditions of imaging procedures, and that the angular distribution of the emission angle intervals is then determined appropriately by the controller.

In another particular embodiment of the invention, the local emission intensity is the same for (and within) all emission angle intervals. Reproduction of the desired angular intensity function is in this case solely achieved via an appropriate angular distribution of the emission angle intervals. This approach has the advantage that the X-ray source can simply be modulated with an ON/OFF behavior (ON within the emission angle intervals, OFF outside).

In general, the desired angular intensity distribution is given in advance according to the particular requirements of the application at hand. In many important examples, the desired angular intensity distribution depends on the object to be irradiated. It may for example have a form such that approximately the same flux of X-rays transmitted through the object (e.g. the body of a patient or an attenuation model thereof) is observed for all viewing angles. This is particularly relevant in case of imaging applications because most X-ray detectors achieve best results at a particular value or range of the incident X-ray flux. The desired angular intensity distribution may for example take into account that an object such as the body of a patient presents sections of different thickness and/or density to an X-ray beam depending on the viewing angle.

The X-ray source may in general be or comprise any means known or suitable for the controllable generation of X-rays. It may for example be an X-ray tube in which accelerated electrons generate X-rays when hitting a target. Moreover, the emission intensity of the X-ray source may be modulated by any appropriate means, for example by controlling the direction or intensity of electrons hitting the target (cf. US 2010/0172475 A1, U.S. Pat. No. 5,696,807), and/or by varying the attenuation of a primary X-ray beam. In a preferred embodiment, the X-ray source may comprise a grid switching tube which has the advantage to provide for a virtually instant pulse rise due to an electronically controlled, in-tube grid switching (cf. WO 2013/001434 A1). This allows for an ON/OFF switching of a given emission with a high frequency. Other suitable technologies for X-ray generation are for example described in the WO 2010/070583 A1, US 2011/0080992 A1, DE 102009051633 A1, DE 102011054114 A1, DE 102011005115 A1, US 2011/0038460 A1, U.S. Pat. No. 6,178,226 B1, US 2011/0103552 A1, or US 2011/0142193 A1.

The X-ray source may optionally be movable with respect to the object (or a site where the object can be located, such as a patient table). The X-ray source may for example be mounted on a gantry that can rotate about the object as it is known from CT scanners.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

In a CT scanner used in clinical applications, the X-ray flux can be modulated during the acquisition to adapt to the actual patient attenuation. Two examples of significant changes in the modulation include the shoulder where the horizontal attenuation (tube at 9 o'clock) can be much larger compared to the tube at 6 o'clock position. Another example is a helical scan moving from the neck to the shoulder of a patient. There are additional applications like Cardiac CT that benefit from flux modulation. Flux may for example be modulated by a modulation of the X-ray tube anode current.

Figure 1:
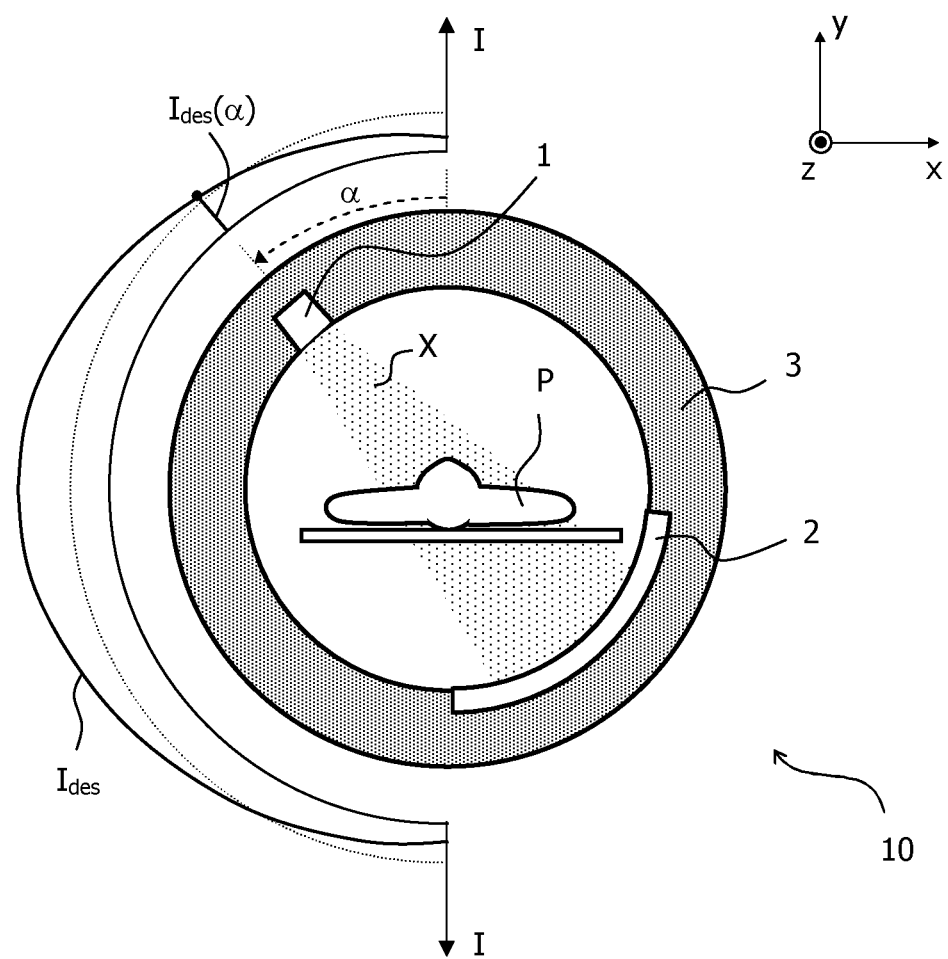
FIG. 1 schematically illustrates the generation of CT images with a given desired angular intensity distribution.

FIG. 1 schematically illustrates this in a section in the x,y-plane through a CT scanner 10. The CT scanner comprises a gantry 3 that can rotate about (a parallel to) the z-axis, i.e. about a patient P lying on a table. The gantry comprises an X-ray source 1 and a detector 2 that are arranged opposite to each other and that can rotate together with the gantry about the patient (alternatively, an extended stationary source and/or detector might be used). During rotation of the gantry, projection images of the patient P from different viewing angles α can be generated.

The flux or intensity of the transmitted X-rays, i.e. at the detector 2, should preferably be within a given range to optimize image quality while minimizing dosage exposure of the patient. To this end, the intensity of the X-ray emission from the X-ray source 1 can be modulated according to a given "desired angular intensity distribution", $I_{des}$. This is illustrated in a polar diagram extending 180° around the gantry. At the depicted angle α, the desired angular intensity distribution has for example the value $I_{des}(\alpha)$, indicating the intensity that should be emitted by the X-ray source 1 at this position.

Figure 2:
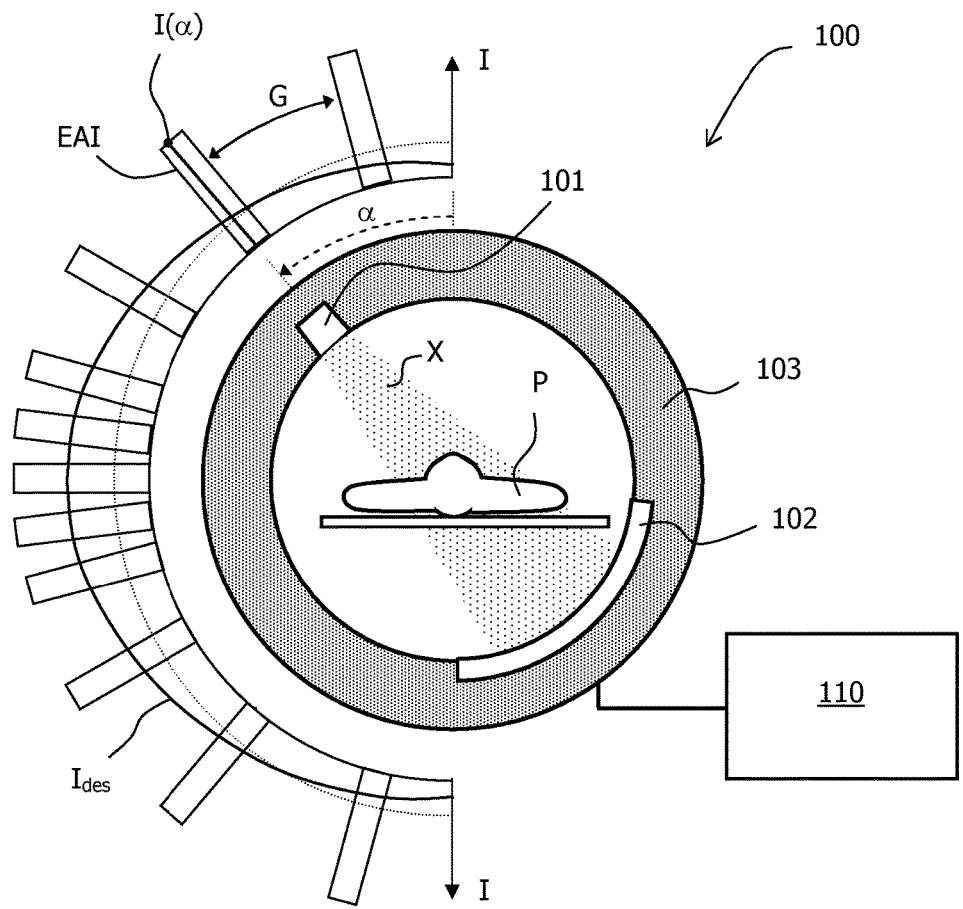
FIG. 2 schematically illustrates the reproduction of a desired angular intensity distribution according to an embodiment of the present invention.

FIG. 2 illustrates the approach of the present invention to reproduce a desired angular intensity distribution $I_{des}$ (having a maximum $I_{des,max}$) and the associated X-ray irradiation apparatus 100, which is in this example also an X-ray CT scanner 100. As above, the CT scanner 100 comprises a rotatable gantry 103 to which an X-ray source 101 and an X-ray detector 102 are attached for generating projection images of a patient P from different viewing angles α. The X-ray source and the detector are connected to a combined controller and reconstruction unit 110 that controls them and that collects and evaluates the imaging data. The X-ray source may particularly be a grid switching tube 101 which allows for rapid switching of the X-ray flux.

In contrast to the situation of FIG. 1, the X-ray emission in FIG. 2 does not take place continuously over a continuous range of viewing angles (e.g. from 0° to 180°), but only at particular "emission angle intervals", EAI, that are separated from each other by gaps G in which no emission occurs.

To reproduce the desired angular intensity distribution $I_{des}$, i.e. to realize a flux modulation as described above, it is proposed to modulate the angular sampling density accordingly. This means that the distribution of emission angle intervals EAI, i.e. their positioning, size, and mutual distance, is adapted by the controller 110 such that the angular average of the emission (at least approximately) matches the desired angular intensity distribution $I_{des}$. In a situation requiring low flux the sampling density will for example be reduced and vice versa. The resulting angular sampling pattern may become non regular. Such data sets can however be reconstructed using iterative reconstruction methods.

The possibility to use e.g. iterative reconstruction allows for a dramatic X-ray dose reduction. The reduction may become so strong, that the X-ray flux seen by the detector 103 becomes very small, which typically leads to the problem that the electronic noise and small signal degradation of the detector become dominant. This problem may be overcome by the above approach, in which X-ray intensities are bundled in the emission angle intervals. The low signal problems of the detector can thus be reduced as a low flux is replaced with stronger short X-ray pulses (with the identical mean flux and dose). As an example, the X-ray flux may be blanked every other measurement interval. The number of angular measurements is then reduced by a factor of two, where each individual measurement has twice the flux as before, to realize the same mean flux. Iterative reconstruction methods can be used for image reconstruction of such sub sampled data without significant loss of image quality.

Figure 3:
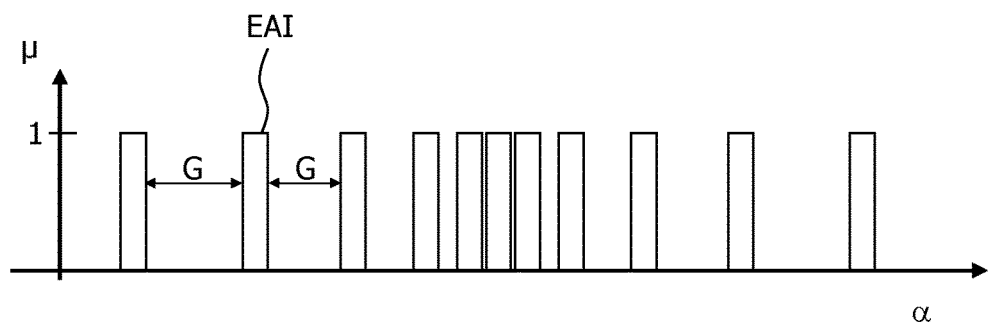
FIG. 3 schematically illustrates the distribution of emission angle intervals and the associated reproduction of a desired angular intensity distribution.
Figure 3:
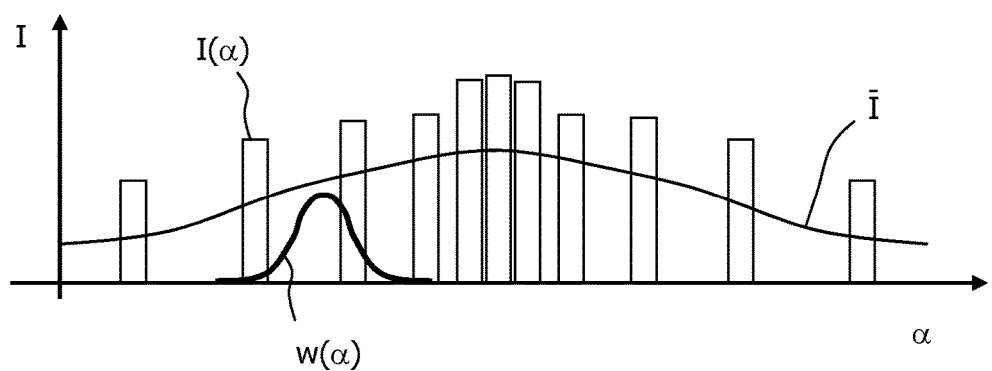

FIG. 3 schematically illustrates the definitions and mathematical procedures applied in the situation of FIG. 2. It should be noted that the emission angle intervals EAI might also have zero width, i.e. they might consist of discrete values.

The top diagram of FIG. 3 shows the distribution of emission angle intervals EAI over the basic range of angles α, extending e.g. from 0° to 180°. The intervals are mathematically described by a membership function $\mu(\alpha)$, having the definition:

$$\mu(\alpha) = \begin{cases} 1 & \text{if } \alpha \in EAI \\ 0 & \text{else} \end{cases}.$$

The bottom diagram of FIG. 3 shows the local emission intensities $I(\alpha)$, which are nonzero only within the above emission angle intervals EAI. The local emission intensity $I(\alpha)$ within a single emission angle interval may be constant or not. In contrast to FIG. 2, the local emission intensities vary in this example between the different emission angle intervals.

The bottom diagram further shows a kernel or weighting function $w(\alpha)$ with which a convolution of the local emission intensities $I(\alpha)$ can be calculated in order to determine the average emission intensity $\bar{I}$ according to the following formula:

$$\bar{I}(\alpha) = \int_{-\infty}^{\infty} w(\alpha-\tau) \cdot I(\tau) d\tau$$

(instead of ±∞, other appropriate integration boundaries might be chosen, e.g. 0 and 180°).

The weighting function $w(\alpha)$ may for example be a Gaussian function $$w(\alpha) = N \cdot \exp(-\alpha^2/2c^2)$$

with a width c and a normalization constant N such that $\int_{-\infty}^{\infty} w(\tau) d\tau = 1$. The width c may for example be chosen as $c = 5\Delta$ with Δ being the mean width of the emission angle intervals, or the mean width of the gaps G. In absolute values, c may typically be chosen between 5° and 90°, preferably between 10° and 30°, e.g. as 20°.

The resulting average emission intensity $\bar{I}$ can be compared to the desired intensity distribution $I_{des}$ (not shown in FIG. 3) to decide whether the latter is "reproduced" or not. A successful reproduction may for example be assumed if the maximal absolute deviation between the two curves in the whole range $[\alpha_{min}, \alpha_{max}]$ of viewing angles is less than p percent of the maximal desired intensity, $I_{des,max}$, with e.g. p=10%. In a formula, this amounts to:

$$\max_{\alpha_{min} \leq \alpha \leq \alpha_{max}} |\bar{I}(\alpha) - I_{des}(\alpha)| / I_{des,max} \leq p$$

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An X-ray imaging apparatus that is adapted to irradiate an object from different viewing angles, comprising:

an X-ray source for emitting X-rays towards the object from said different viewing angles;

a detector for detecting X-rays emitted by the X-ray source and for generating projection images of the object from said different viewing angles;

a reconstruction module for reconstructing sectional images of the object from said projection images;

a controller for controlling the X-ray source such that emissions occur only at emission angle intervals separated by gaps, wherein the angular distribution of these emission angle intervals and the associated local emission intensity are determined by the controller to at least approximately reproduce, in the angular mean, a desired angular intensity distribution given for all viewing angles, wherein the emission angle intervals include at least three emission angle intervals within 180 degrees; wherein sizes of the gaps between the at least three emission angle intervals vary.

2. A method for generating images of an object by irradiating said object with X-rays from different viewing angles, said method comprising:

the emission of X-rays towards the object only from emission angle intervals that are separated by gaps, wherein the angular distribution of these emission angle intervals and the associated local emission intensity are determined to at least approximately reproduce, in the angular mean, a desired angular intensity distribution given for all viewing angles, wherein the emission angle intervals include at least three emission angle intervals within 180 degrees, wherein sizes of the gaps between the at least three emission angle intervals vary;

generating projection images of the object by the X-rays emitted from said different viewing angles;

reconstructing sectional images of the object from said projection images.

3. The imaging apparatus according to claim 1 or the method according to claim 2, characterized in that the local emission intensity is larger than a given minimal intensity.

4. The imaging apparatus according to claim 1 or the method according to claim 2, characterized in that local emission intensity is the same for all emission angle intervals.

5. The imaging apparatus according to claim 1 or the method according to claim 2, characterized in that the desired angular intensity distribution is such that approximately the same flux of X-rays transmitted through the object is observed for all viewing angles.

6. The imaging apparatus according to claim 1, characterized in that the X-ray source comprises a grid switching tube.

7. The imaging apparatus according to claim 1, characterized in that the X-ray source is movable with respect to the object.

8. The imaging apparatus according to claim 1, wherein the reconstructed sectional images are volumetric slice images.

9. The imaging apparatus according to claim 1, wherein local emission intensity of each of the at least three emission angle intervals vary.

10. The imaging apparatus according to claim 1, wherein local emission intensity of each of the at least three emission angle intervals are the same.

* * * * *